US006778850B1

(12) United States Patent
Adler et al.

(10) Patent No.: US 6,778,850 B1
(45) Date of Patent: *Aug. 17, 2004

(54) FRAMELESS RADIOSURGERY TREATMENT SYSTEM AND METHOD

(75) Inventors: John R. Adler, Stanford, CA (US); Achim Schweikard, Hamburg (DE)

(73) Assignee: Accuray, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/663,104

(22) Filed: Sep. 15, 2000

Related U.S. Application Data

(63) Continuation-in-part of application No. 09/270,404, filed on Mar. 16, 1999, now Pat. No. 6,144,875.

(51) Int. Cl.[7] .................................................. A61B 6/00
(52) U.S. Cl. ........................ 600/427; 600/429; 378/4; 606/130
(58) Field of Search ................................ 600/427, 429, 600/439, 437, 428, 425, 426, 407; 378/69, 205, 196, 197, 198, 4; 356/375; 606/130

(56) References Cited

U.S. PATENT DOCUMENTS

| | | | | |
|---|---|---|---|---|
| 5,207,223 A | * | 5/1993 | Adler ....................... 128/653.1 |
| 5,427,097 A | * | 6/1995 | Depp ....................... 128/653.1 |
| 5,446,548 A | * | 8/1995 | Gerig et al. ................. 356/375 |
| 5,727,554 A | * | 3/1998 | Kalend et al. .............. 600/407 |
| 5,748,700 A | * | 5/1998 | Shepherd et al. ............. 378/65 |
| 5,797,849 A | * | 8/1998 | Vesely et al. ............... 600/461 |
| 6,019,724 A | * | 2/2000 | Gronningsaeter et al. ... 600/439 |
| 6,031,888 A | * | 2/2000 | Ivan et al. .................... 378/20 |
| 6,144,875 A | * | 11/2000 | Schweikard et al. ........ 600/427 |
| 6,149,592 A | | 11/2000 | Yanof et al. |
| 6,256,372 B1 | | 7/2001 | Aufrichtig et al. |
| 6,285,902 B1 | | 9/2001 | Kienzle, III et al. |
| 6,301,495 B1 | * | 10/2001 | Gueziec et al. ............. 600/407 |
| 6,405,072 B1 | * | 6/2002 | Cosman ..................... 600/426 |
| 6,470,207 B1 | | 10/2002 | Simon et al. |
| 2002/0032453 A1 | * | 3/2002 | Cosman ..................... 606/130 |
| 2002/0065461 A1 | * | 5/2002 | Cosman ..................... 600/426 |
| 2002/0154728 A1 | | 10/2002 | Morita et al. |

* cited by examiner

*Primary Examiner*—Eleni Mantis Mercader
(74) *Attorney, Agent, or Firm*—McDermott Will & Emery LLP

(57) ABSTRACT

A method and apparatus for selectively and accurately localizing and treating a target within a patient are provided. A three dimensional mapping of a region surrounding the target is coupled to a surgical intervention. Two or more diagnostic beams at a known non-zero angle to one another may pass through the mapping region to produce images of projections within the mapping region in order to accurately localize and treat the target wherein the images are captured using one or more image recorders.

21 Claims, 12 Drawing Sheets

SYSTEM BLOCK DIAGRAM

FRAMELESS RADIOSURGERY TREATMENT SYSTEM AND METHOD

RELATED APPLICATION

This application is a continuation in part of U.S. patent application Ser. No. 09/270,404, filed Mar. 16, 1999 now U.S. Pat. No. 6,144,875 entitled "Apparatus and Method for Compensating for Respiratory and Patient Motion During Treatment" which is owned by the same assignee as the present invention and is incorporated herein by reference.

BACKGROUND OF THE INVENTION

This invention relates generally to a system and method for treating a patient and in particular to a system and method for controlling a treatment to administer a precise dose to a patient. In more detail, the invention relates to an apparatus and method for performing accurate surgical procedures on a particular target region within a patient utilizing previously obtained reference data indicating the position of the target region with respect to its surrounding which may contain certain reference points.

In order to control a surgical procedure, such as radiosurgery, many different prior techniques have been used including the manual targeting of the treatment. Many of the prior techniques are not sufficiently accurate so that healthy tissue surrounding the target region is often unnecessarily irradiated and damaged or killed. Other techniques are clumsy and cannot be used for particular types of treatments. For example, one prior technique involved frame-based stereotaxy that was often used for body parts and regions that could be easily physically immobilized. For example, the frame based stereotaxy was often used to immobilize the head of the patient so that a target region in the brain, such as a brain tumor, could be irradiated by the radiosurgical beam. To do so, the patient was positioned on a treatment bed and then his/her head was immobilized by a frame that was securely attached to the person's head with some attachment means and that was also securely attached to an immovable object such as a treatment table. Thus, during the treatment, the patient was not able to move his/her head at all which permitted an accurate targeting of the treatment. The problem is that a frame-based system cannot be used for fractionated treatment in which repeated smaller dose are given to the patient over some predetermined period of time, such as a couple of weeks or a month. A fractionated treatment plan is often desirable since it permits larger overall doses of treatment, such as radiation, to be applied to the target region while still permitting the healthy tissue to heal. Clearly, it is extremely difficult to leave the frame secured to the patient's head for that period of time. In addition, it is impossible to remove the frame and later reposition the frame in the exact same location for the next treatment. Thus, the frame based stereotaxy provides the desired accuracy, but cannot be used with various desirable treatment schedules.

Another typical positioning system is a frameless stereotaxy system wherein a physical frame attached to the patient is not necessary. An example of a frameless stereotaxy system is disclosed in U.S. Pat. No. 5,207,223 which is owned by the same assignee as the present invention and is incorporated herein by reference. In general, a preoperative imaging of the region surrounding the target region is completed, such as by computer tomography. Then, during the treatment, a stereo image is generated, such as by X-ray imaging. The stereo image is then correlated to the preoperative image in order to locate the target region accurately. Then, a radiation source located on a robot is automatically positioned based on the correlation between the preoperative scans and the stereo images in order to accurately treat the target region without unnecessarily damaging the healthy tissue surrounding the target region.

The current frameless stereotaxic techniques have some limitations which limit their effectiveness. First, most surgical operation rooms have limited workspace and the current stereotaxic frameless systems require a large space due to the movement of the robot supporting the surgical radiation beam and the two beam imagers. Second, the cost of having two beam generators and two imagers is very high making the treatment system very expensive. These systems also typically require some form of implanted fiducials, such as markers that are viewable using an X-ray, to track soft tissue targets. Finally, for most current frameless systems, breathing and other patient motion may interfere with the target region identification and tracking due to a degradation of the images. Thus, it is desirable to provide a frameless radiosurgery treatment system and method that overcomes the above limitations and problems and it is to this end that the present invention is directed.

SUMMARY OF THE INVENTION

A method and apparatus for selectively and accurately localizing and treating a target within a patient are provided. A three dimensional mapping of a region surrounding the target is coupled to a surgical intervention. Two or more diagnostic beams at a known non-zero angle to one another may pass through the mapping region to produce images of projections within the mapping region in order to accurately localize and treat the target.

To accomplish the accurate positioning and targeting, a three-dimensional ("3-D") mapping of the patient is generated for a portion of the patient's body having the target region and stored as reference data. Then, two or more diagnostic beams are passed through the mapping region wherein the beams are at predetermined non-zero angle with respect to each other. A single image camera or recording medium may be used to capture the images from the one or more diagnostic beams such as shown in U.S. Pat. No. 5,207,223 to Adler. In more detail, the single image camera or recording medium may be segmented into one or more pieces so that the image from the first diagnostic beam is captured on a first piece of the recording medium, the image from the second diagnostic beam is captured on a second piece of the recording medium, the images are downloaded to a computer and then images from the subsequent diagnostic beams are captured.

Once the diagnostic images are generated, they are compared to the stored 3-D reference data to generate information about the patient and the location of the target region as is known from the Adler patent. At predetermined small time intervals, the diagnostic images are obtained and compared to the reference data. The results of the comparison may be used to adjust the targeting of the treatment beam on the target region to ensure that the dose of the surgical treatment beam remains focused on the target region. This results in a more accurate treatment so that fewer healthy cells and tissue are damaged by the treatment which results in fewer complications following the treatment and permits more aggressive and effective treatments.

In accordance with a first embodiment of the invention, there may be a diagnostic beam device or one or more diagnostic beam devices and a single recording medium underneath the patient or close to the patient couch. In one embodiment, the single diagnostic beam device moves in a predetermined manner to predetermined different positions so that the diagnostic beam, at each position, passes through the target region at predetermined angles. Thus, each image generated by the diagnostic beam device is at a predetermined non-zero angle with respect to the other images. Once the diagnostic images are generated, the above treatment control process is used.

In accordance with a preferred embodiment of the invention, a diagnostic beam device is used and a recording medium is located underneath the patient as described above. In this embodiment, the diagnostic images of the target region, formed by moving the diagnostic beam device, are gated with respect to real-time measurement of involuntary patient motion, such as respiration or pulsation. Thus, in this embodiment, the motion is compensated for as the treatment of the patient occurs and the images acquired by the diagnostic beams are not degraded by the movement of the target region.

The series of diagnostic beam images formed by the moving diagnostic beam generates a rough computer tomography (CT) scan of the patient that may be compared to the more precise pre-operative CT scan. In addition, the diagnostic beams and treatment beam may be energized and triggered during predetermined times during the respiration cycle of the patient to ensure accurate positioning of the target region.

Thus, in accordance with the invention, a system for directing a treatment beam towards a patient is provided. The system may comprise a treatment bed that supports the patient during the treatment and one or more diagnostic beam generators for generating diagnostic beams towards the patient during the treatment. The diagnostic beam generators may be located at different predetermined positions so that the beam from each diagnostic beam generator is at a predetermined non-zero angle with respect to the beams of the other diagnostic beam generators. The system may further comprise a single image recording device located adjacent to the treatment bed for receiving the diagnostic beams from the two or more diagnostic beam generators so that the image recording device captures the images from all of the diagnostic beams.

In accordance with another aspect of the invention, a system for directing a treatment beam towards a patient is provided that comprises a treatment bed that supports the patient during the treatment and a diagnostic beam generator for generating a diagnostic beam directed towards the patient during the treatment. The system further comprises a track that supports the diagnostic beam generator to move the diagnostic beam generator between one or more different positions so that the beam from each diagnostic beam generator is at a predetermined non-zero angle with respect to the beam of the diagnostic beam generator at a different position. The system further comprises one or more image recording device(s) located adjacent to the treatment bed for receiving the diagnostic beams from the diagnostic beam generator at the different positions in a sequential manner so that the image recording device captures the images from all of the diagnostic beams.

In accordance with yet another aspect of the invention, a method for treating a patient is provided wherein a three-dimensional mapping of a region of the patient including a target region to be treated by a treatment beam is utilized and one or more diagnostic beams directed towards the patient are generated. Then, one or more images are captured in one or more image recorder(s) when the diagnostic beams pass through the target region of the patient wherein the diagnostic beams pass through the patient at non-zero angles with respect to each other. Finally, the images from the diagnostic beams and the three-dimensional mapping are compared in order to control the movement of the treatment beam during the treatment.

To perform the comparison, the intra-treatment/live images are correlated to the pre-operation data as is well known. The pre-operative data provides spatial information on the relative placement of the anatomical structures from which the current intra-treatment position of the target region may be computed. To compute the target region position, the correlation method may comprise deforming the pre-operative data so that it optimally corresponds to the intra-treatment image data, or vice versa so that the deformation of the intra-treatment data better matches the pre-operative data.

DETAILED DESCRIPTION OF A PREFERRED EMBODIMENT

The invention is particularly applicable to a radiosurgical treatment system and method and it is in this context that the invention will be described. It will be appreciated, however, that the system and method in accordance with the invention has greater utility, such as to other types of treatments wherein it is necessary to accurately position a treatment at a target region within the patient in order to avoid damaging healthy tissue such as to other types of medical procedures with other types of medical instruments, such as positioning biopsy needles, ablative, ultrasound or other focused energy treatments, positioning a laser beam for laser beam treatment or positioning radioactive seeds for brachytherapy. Prior to describing the invention, a typical radiosurgery device will be described to provide a better understanding of the invention.

Figure 1:
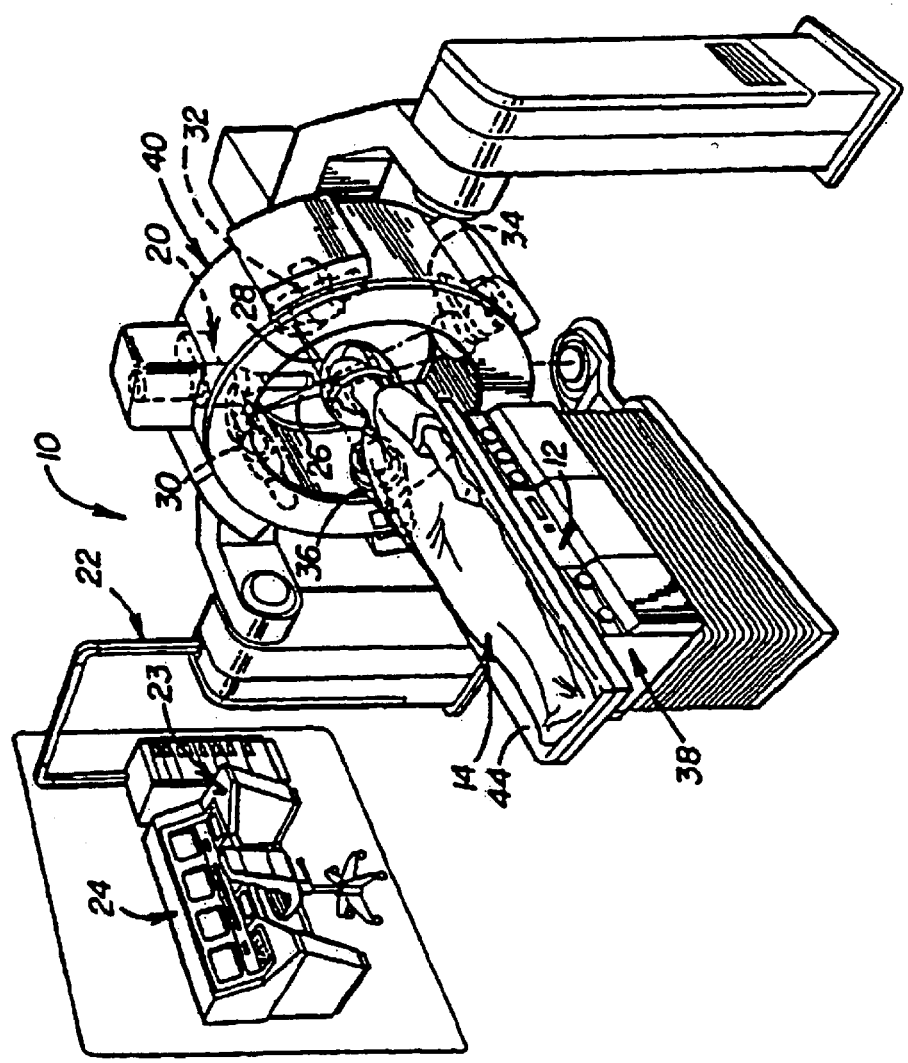
FIG. 1 is a diagram illustrating a typical frameless radiosurgical treatment system.
Figure 2:
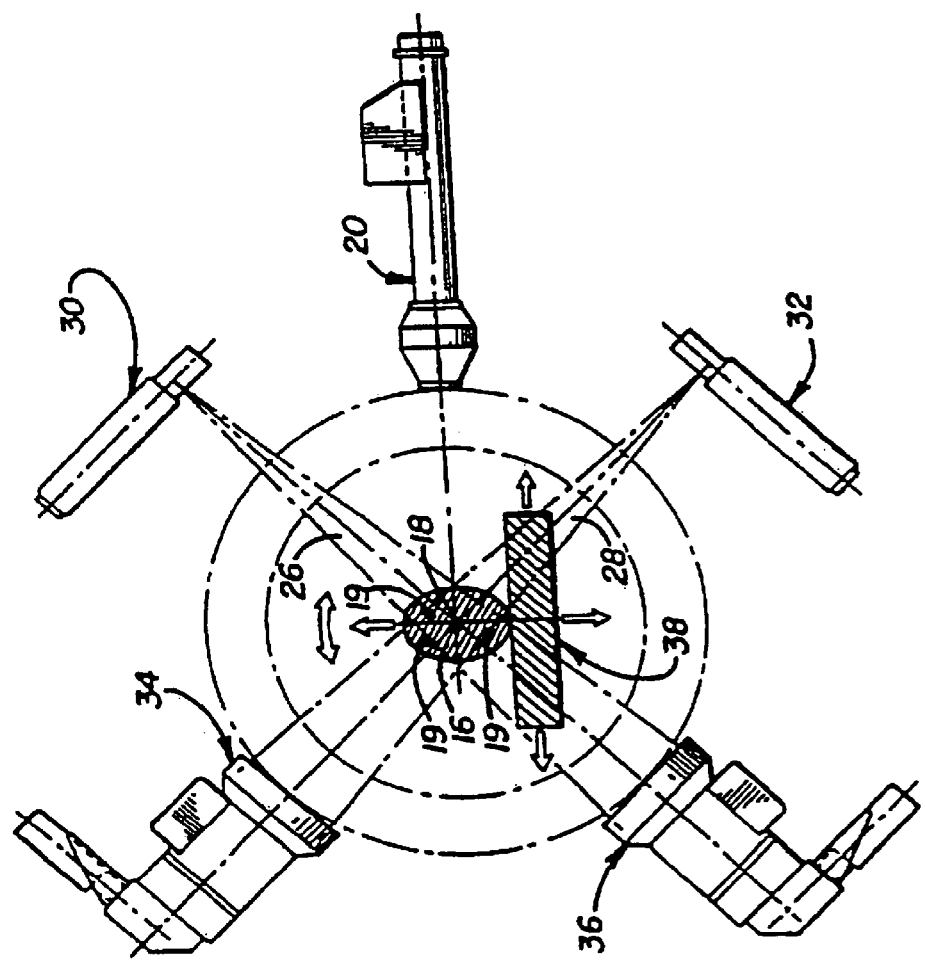
FIG. 2 is a diagram illustrating the diagnostic and treatment beams of the system shown in FIG. 1.
Figure 3:
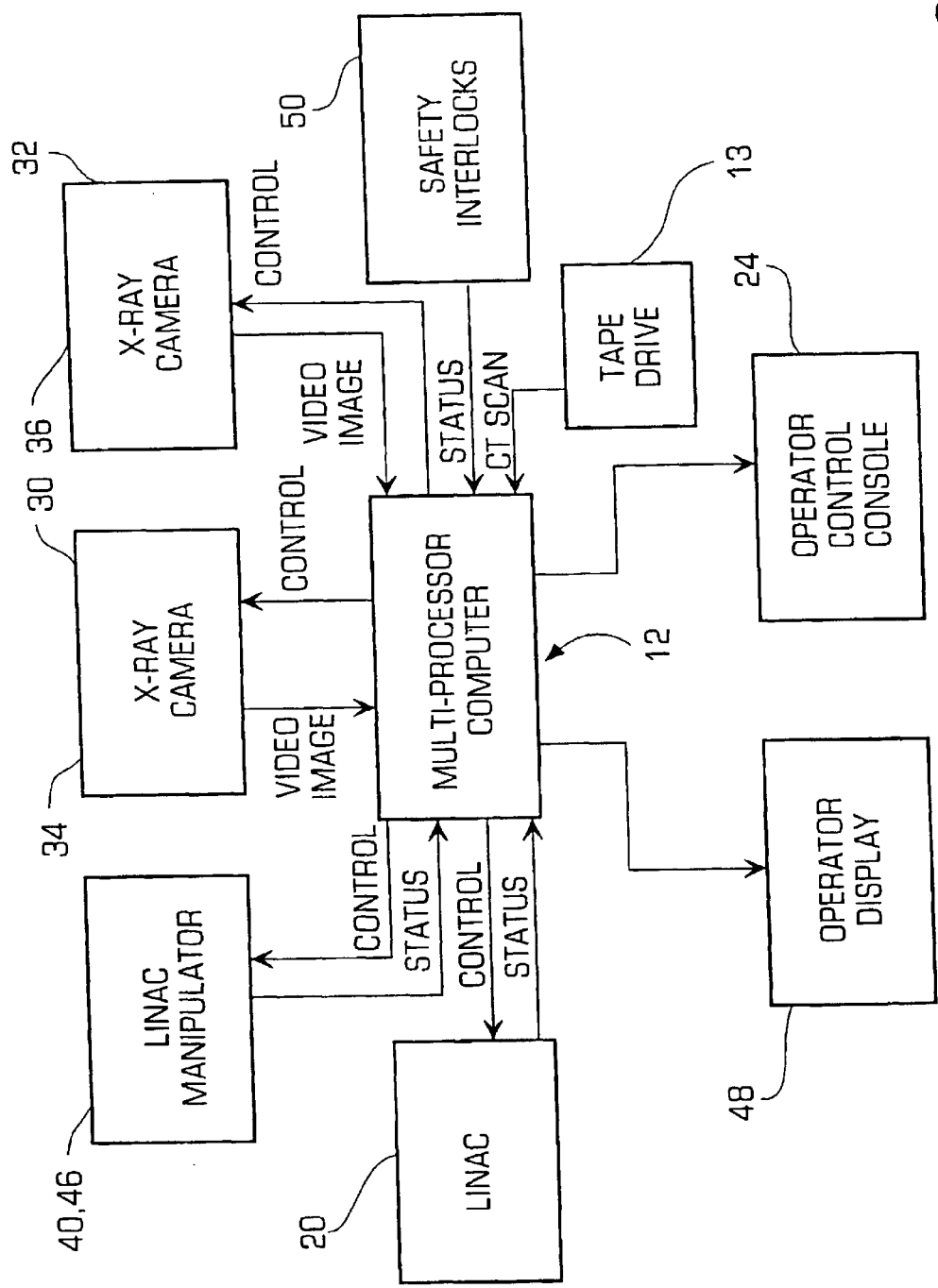
FIG. 3 is a block diagram illustrating the treatment system of FIG. 1.

FIGS. 1–3 are diagram illustrating an example of a stereotaxic radiation treatment device 10. The radiation treatment device 10 may include a data processor 12, such as a microprocessor, and a disc or tape storage unit 13 (shown in FIG. 3) which may store a three dimensional image of a patient 14. The three dimensional image may be loaded into the data processor, if not already there, to compare the three dimensional image to images generated during the surgical procedure. The three dimensional image may be generated by various conventional techniques such as computer aided tomography (CAT) scan or magnetic resonance imaging (MR). The radiation treatment device 10 may also include a beaming apparatus 20 which, when activated, emits a collimated surgical ionizing beam directed at a target region 18 (shown in FIG. 2). The collimated surgical ionizing beam may have sufficient strength to cause the target region to become necrotic. A variety of different beaming apparatus may be used which generate an ionizing radiation or heavy particle beam such as a linear accelerator and preferably an x-ray linear accelerator. Such an x-ray beaming apparatus is commercially available. The beaming apparatus may be activated by the operator throwing a switch 23 at a control console 24 connected to the beaming apparatus 20 by a cable 22.

Figure 4:
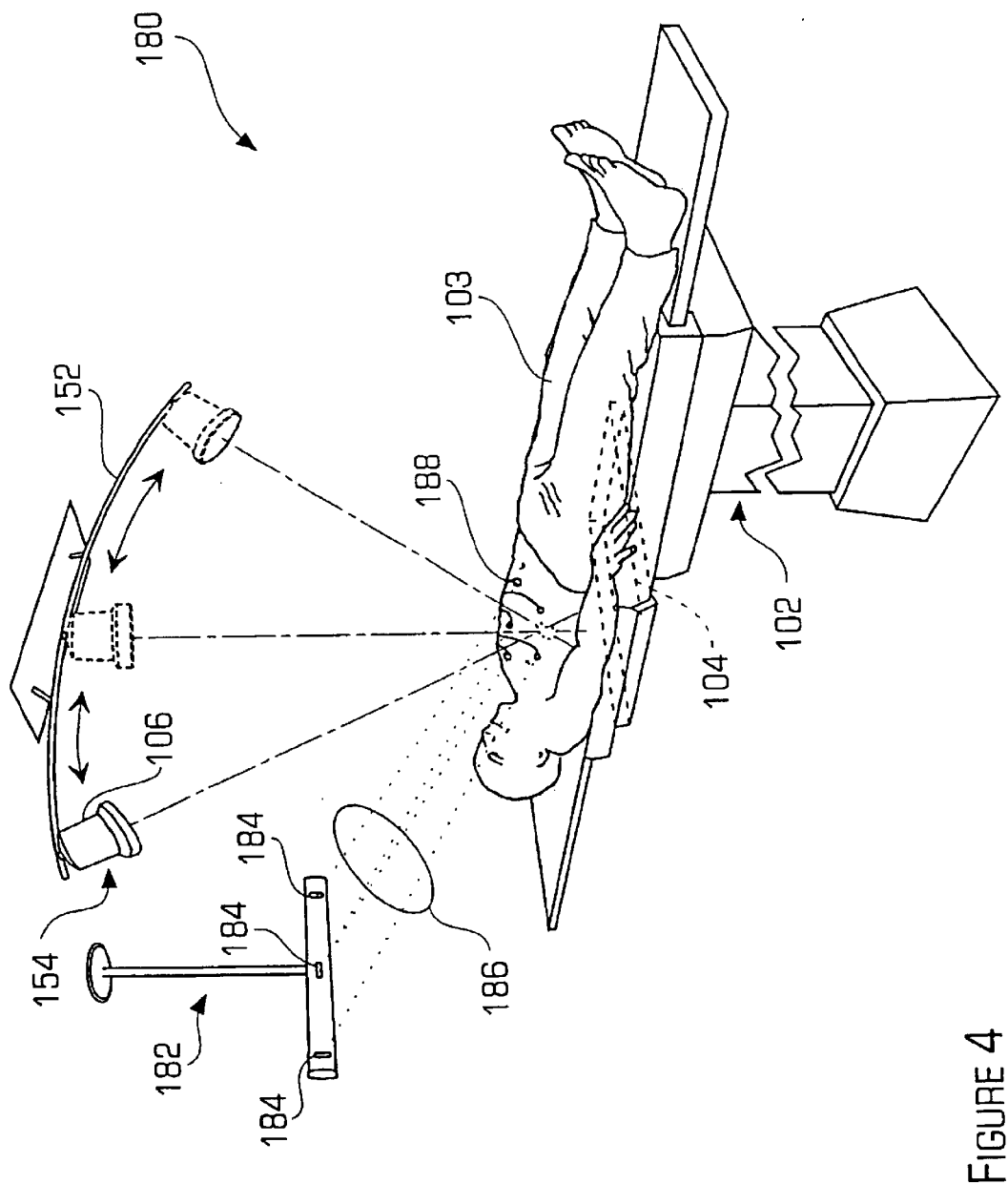
FIG. 4 is a diagram illustrating a preferred embodiment of the frameless treatment system in accordance with the invention.

The radiation treatment device 10 may also include an apparatus for passing a first diagnostic beam 26 and a second diagnostic beam 28 through the region previously imaged by the three-dimensional image. The diagnostic beams are positioned at a predetermined non-zero angle with respect to each other, such as being orthogonal as shown in FIG. 2. The diagnostic beams may be generated by a first x-ray generator 30 and a second x-ray generator 32, respectively. A first and second image receiver 34, 36 or a single receiver may receive the diagnostic beams 26, 28 to generate an image from the diagnostic beams which is fed into the microprocessor 12 (as shown in FIG. 4) so that the diagnostic images may be compared to the three-dimensional image.

The radiation treatment device 10 may also include a device for adjusting the relative positions of the beaming apparatus 20 and/or the patient 14 so that the ionizing beam is continuously focused on the target region 18. In the radiation treatment device shown in FIG. 1, the positions of the beaming apparatus and the patient may be altered with six degrees of freedom by a gantry 40 and a moveable operating table 38 with a tilting top 44. The positions of the beaming apparatus relative to the patient may also be accomplished by using a processor controllable robotic arm mechanism that permits the beaming apparatus to be moved freely about the patient's body including up, down, longitudinally along or laterally along the body of the patient.

FIG. 3 is a block diagram of the radiation treatment device 10 including the microprocessor 12, the tape drive 13, the beaming apparatus 20, the robotic arm 46 or the gantry 40, the x-ray cameras 30, 32, 34 and 36, and the operator control console 24 as described above. In addition, the device 10 may include safety interlocks 50 to ensure that the beaming apparatus is not activated accidentally. The device 10 may also include an operator display 48 for tracking the progress of the treatment and controlling the treatment. Any further details of the radiosurgery device may be found in U.S. Pat. No. 5,207,223 which is owned by the assignee of this application and which is incorporated herein by reference.

The above system is well suited for the treatment of stationary target regions (e.g., stationary with respect to bony structures that can be seen on an image) wherein respiratory motion or pulsation motion do not affect the accuracy of the treatment beam. The drawback of the above system is that anatomic sites subject to respiratory motion are difficult to treat. In accordance with the invention, the frameless treatment system may improve upon the system shown in FIGS. 1–3. The frameless treatment system and method in accordance with the invention with the above advantages will now be described.

FIG. 4 is a diagram illustrating a preferred embodiment of the frameless treatment system 180 in accordance with the invention. This embodiment of the invention is particular applicable to the targeting of a target region without embedded markers wherein there is no surrounding region that can be easily located (e.g., no bones are present) and respiration motion may affect the position of the target region. An example of a target region for this embodiment is a lung tumor.

The treatment system 180 may include a patient treatment table or couch 102 on which a patient 103 may rest during the treatment. The treatment system may also include a diagnostic beam recording device 104 that may be located underneath the treatment table and underneath the patient and one or more diagnostic beam generators 106 (one is shown in this example). The recording device 104 may record the images generated when the diagnostic beam device is energized at one or more different predetermined positions. The recording device 104 may be any device that can be used to capture the image generated by the diagnostic beams. In a preferred embodiment, the recording device 104 may be the amorphous silicon plate that captures the x-ray beams being generated by the diagnostic beam generators 106. The recording device 104 may be connected to a computer that controls the operation of the recording device and the diagnostic beam generator. The recording device in this embodiment may also have a first portion 105 and a second portion 107 wherein the first diagnostic beam is captured by the first portion and the second diagnostic beam is captured by the second portion. Thus, the diagnostic beams may be simultaneously energized or may be sequentially energized. A recording medium with one or more diagnostic beams is also shown in U.S. Pat. No. 5,207,223 to Adler which is owned by the same assignee as the present invention.

The robot and the treatment beam generator (shown in FIG. 5) are not shown in FIG. 4. The system may further include a track 152 in which the diagnostic beam generator moves so that the diagnostic beam generator may be moved to different positions (see the diagnostic beam generator 106 in a first position 154 and the other positions shown by the phantom pictures of the generator) wherein the diagnostic beam generator is at a different non-zero angle with respect to the other positions. Thus, in this embodiment, the diagnostic beam generator 106 is moved from the first position 154 to other positions at periodic times in order to generate the images of the target region as described above. In addition to the elements shown in FIG. 5, the system may also include a controller, to position of the diagnostic beam generator, that may be controlled by the computer.

In addition to the above, this system 180 may also include an external marker tracking device 182 that may include one or more external marker tracking generators 184 that generate one or more external marker tracking beams 184, such as infrared beams or passive markers whose position is detectable with optical cameras. The system may also include one or more external markers 188 attached to the patient that measure the external movement of the patient during respiratory motion as described in more detail in the co-pending application that was incorporated by reference. Now, the system will be described in more detail.

Figure 5:
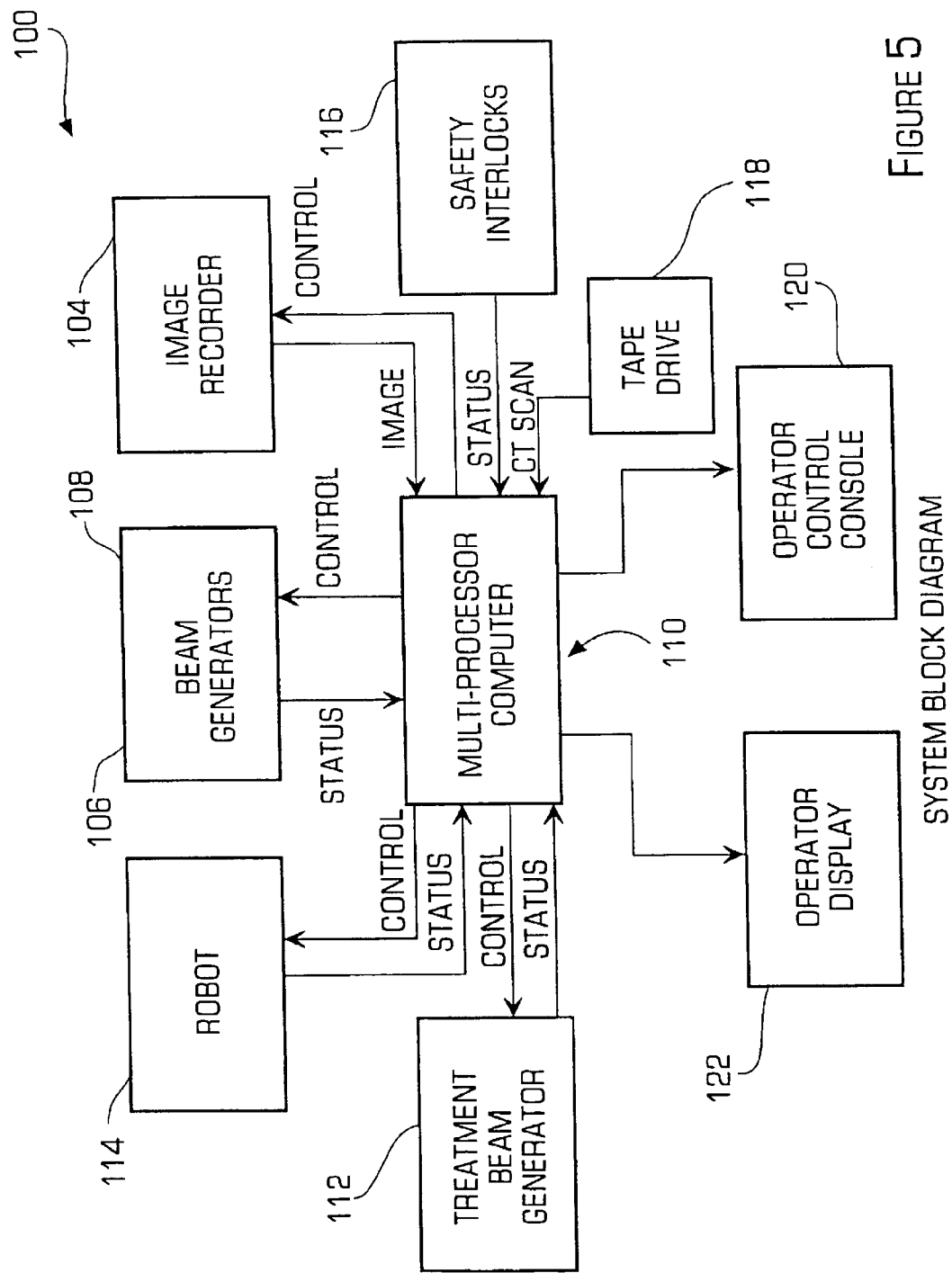
FIG. 5 is a block diagram illustrating more of the details of the treatment system of FIG. 4.

FIG. 5 is a block diagram illustrating more of the details of the treatment system 100 of FIG. 4. In particular, the system 100 may include a computer 110 that controls the operation of the various elements of the system including the beam generators 106, 108 as well as the image recorder 104. The system may also include a treatment beam device 112, such as a linear accelerator (LINAC) in this embodiment, that generates a treatment beam and a robot 114 that positions the treatment beam (a LINAC manipulator in this embodiment) that are both controlled by the computer 110 that may be a multi-processor computer in this embodiment. The computer may issue control commands and receive back status commands from the treatment beam generator 112, the robot 114 and the beam generators 106, 108. For the image recorder 104, the computer may issue control signals to control the operation of the image recorder as described above and may receive image data from the image recorder.

The system may also include safety interlocks 116 that ensures that the diagnostic beams and the treatment beam cannot be activated (the beams are only energized when a status signal is received by the computer) unless all people other than the patient are out of the treatment room due to the radiation danger. The system may also include a tape drive 118 for storing the images generated by the image recorder, the pre-operative CT three-dimensional images and any treatment planning software that may perform the comparison of the images and control the movement of the treatment beam. The system may further include an operator control console 120 and an operator display 122 that permit a user of the system, such as a surgeon, to interact with and operate the system and monitor the treatment. The treatment planning software in the computer may compare the pre-operative image to the images from the diagnostic beam generators to determine how to control the treatment robot and therefore the treatment beam during the treatment. The computer, based on the comparison and the surgeon's manual commands, may then control the treatment beam in order to deliver the appropriate dose to the patient without damaging the healthy tissue surrounding the target region. Now, a method of treatment using the preferred embodiment will be described.

Figure 6:
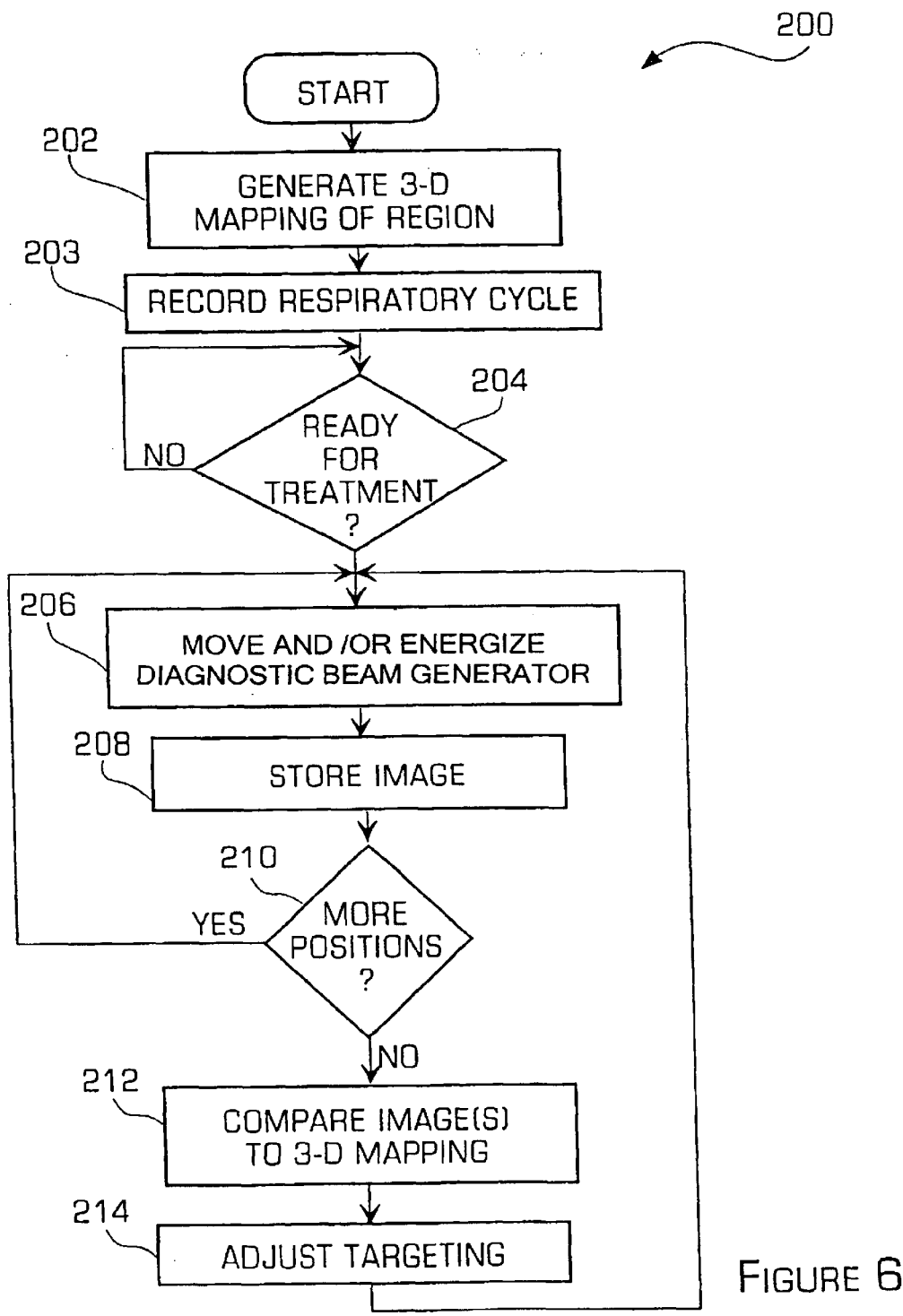
FIG. 6 is a flowchart illustrating a method for treatment in accordance with the invention using the system of FIG. 4.

FIG. 6 is a flowchart illustrating a method 200 for treatment in accordance with the invention using the system of FIG. 4. In step 202, a three-dimensional mapping of a region of the patient including the target region is generated prior to the treatment. The three-dimensional mapping may be done using typical equipment such as computer tomography, magnetic resonance tomography or the like. The three-dimensional mapping of the region is stored in the storage device 118. The mapping shows the relative locations of the target region with respect to other surrounding regions that may be seen in the mapping to locate the target region relative to the surrounding regions. For example, the target region may be a lung tumor.

Figure 9:
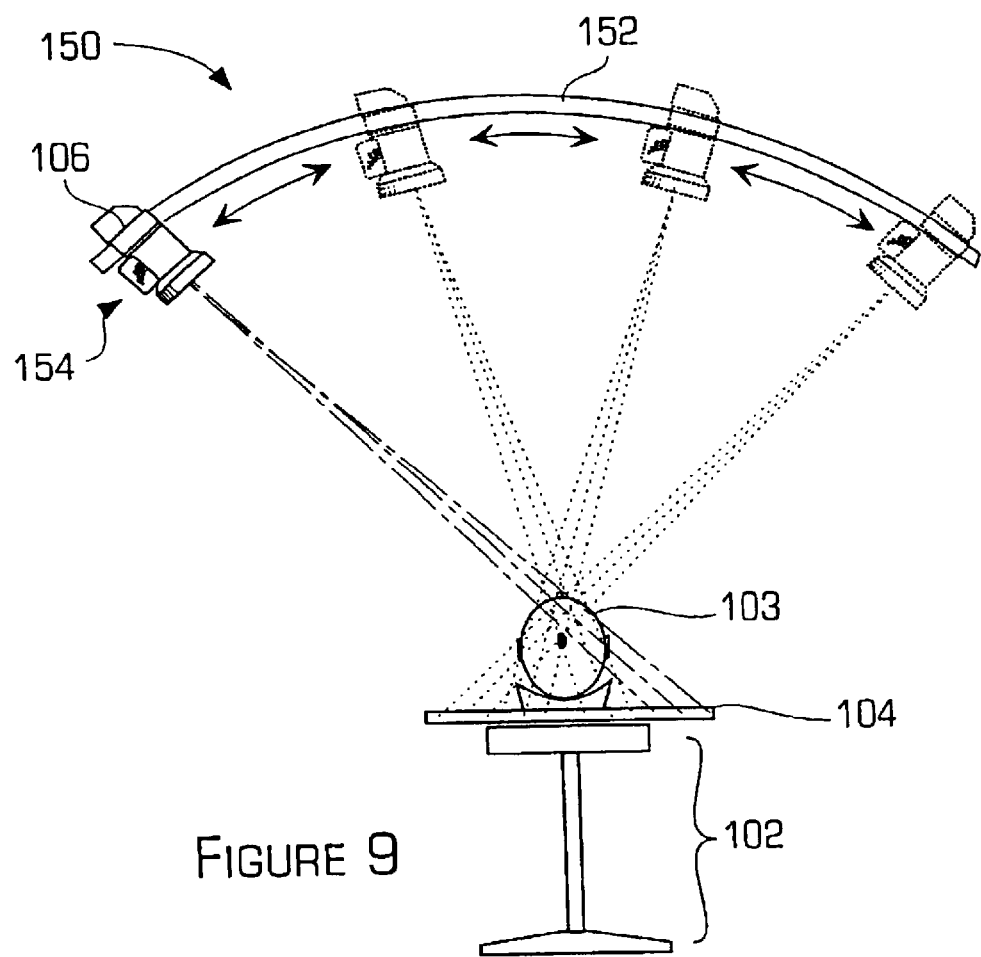
FIG. 9 is a diagram illustrating a second embodiment of the frameless treatment system in accordance with the invention.

On the day of treatment, the patient may be positioned on the treatment bed as shown in FIG. 9. The respiratory cycle of the patient may then be determined in step 203 and at various different times during the treatment. The respiratory cycle may be determined by monitoring chest wall surface movement with optical or ultrasound digitizers, and/or by using a strain gauge, by the measurement of the airflow exiting the patient or by other well known methods. In step 204, the system may determine if the treatment can begin based on the status of the safety interlocks. If it is not safe to begin the treatment, then the method loops back to test the safety interlocks until a safe condition is indicated.

In step 206, a diagnostic beam generator is positioned along the track in the appropriate position and energized by the computer in order to generate an image on the recording device. In a preferred embodiment, the diagnostic beam generator is an x-ray generators and the image recorder is an amorphous silicon imager that generates an image in response to x-rays as is well known. The image generated by the first diagnostic beam in the image recorder may then be downloaded by the computer to the storage device attached to the computer in step 208 and the image recorder may be reset. Each image is acquired at the same phase of the respiratory cycle as described below with respect to FIGS. 7 and 8.

In step 210, the method determines if there are any other positions for the diagnostic beam. If there are other positions for the diagnostic beam, the method loops back to step 206 to energize that generator at the other position, generate an image and download the image to the storage device. In this embodiment, the movement of the diagnostic beam generator along the track generates multiple images wherein each image is at a non-zero angle with respect to the other images and acquired during the same phase of the respiratory cycle. In accordance with the invention, the method sequentially energizes the diagnostic beam generator at different positions to generate the images in a sequential manner. In accordance with the invention, repeated sequence of images from the diagnostic beam generator may be generated at periodic times so that the location of the target region at different times may be determined.

The series of diagnostic beam images may be processed using a CT-like algorithm to generate a 3-D image of the patient during the treatment. Once the series of diagnostic images are processed into a 3-D image, the 3-D image is compared to the three-dimensional pre-operative mapping as is well known to determine the location of the target region at the particular time in step 212. In step 214, the targeting of the treatment beam is adjusted based on the comparison so that the treatment beam is always focused on the target region. If there are repeated diagnostic images generated, after each new set of images is generated, the images are compared to the mapping and the treatment beam targeting is adjusted to compensate for changes in the position of the target region. In this manner, the target region is accurately tracked so that the treatment beam is focused on the target region.

In some cases, the placement of certain structures is visible in the intra-treatment 3-D reconstruction, but the target region or critical region is either not visible at all, not clearly visible, or is visible but difficult to segment automatically by computer. In this case, the system may comprise the step of deforming the intra-treatment images in such a way that the positions of the clearly visible structures best match the pre-operative image data. From this, the exact deformation pattern of the entire anatomical area can be inferred. The exact position of the target and/or healthy critical tissue visible in the pre-operative image data, but not clearly visible in the intra-treatment data may be inferred as described in more detail with reference to FIG. 13.

Figure 7:
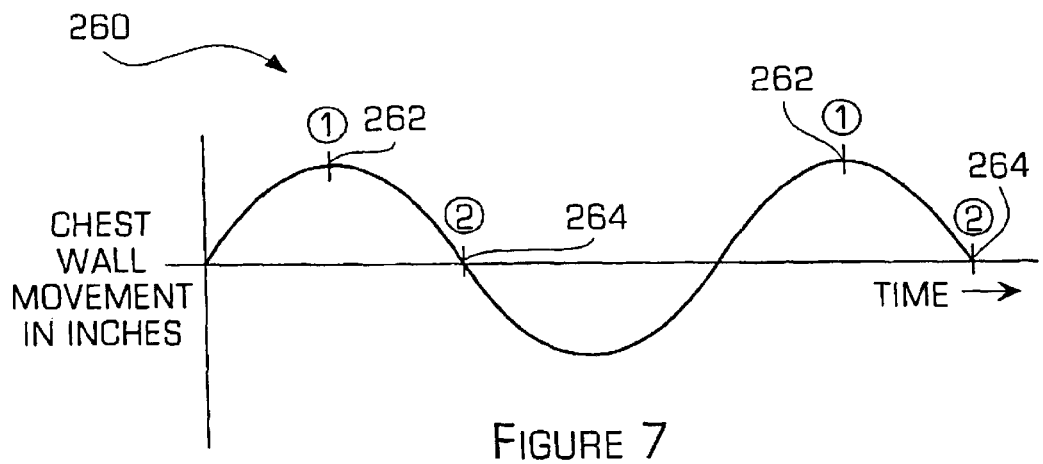
FIG. 7 is a diagram illustration a respiration cycle of a patient.

FIG. 7 is a chart 260 illustrating a typical respiration cycle for a human being wherein the respiration cycle is represented by a sine wave. The y-axis of the chart is the movement of the chest wall thus showing that the chest wall moves out and in during the respiration cycle. A first point 262 in the respiration cycle with maximum expansion of the chest and a second point 264 in the respiration cycle with no chest movement are shown. The respiration cycle may be determined using the various techniques described above. In accordance with the invention, the energizing of the diagnostic beams and the treatment beam may be periodically timed so that the energizing occurs at the corresponding points in the respiration cycle such as at the first point or the second point. In addition, the energizing of the beams may occur at more than one time during the respiration cycle. Thus, the accuracy of the treatment is improved since the beams are energized at the same time in the respiration cycle.

Figure 8:
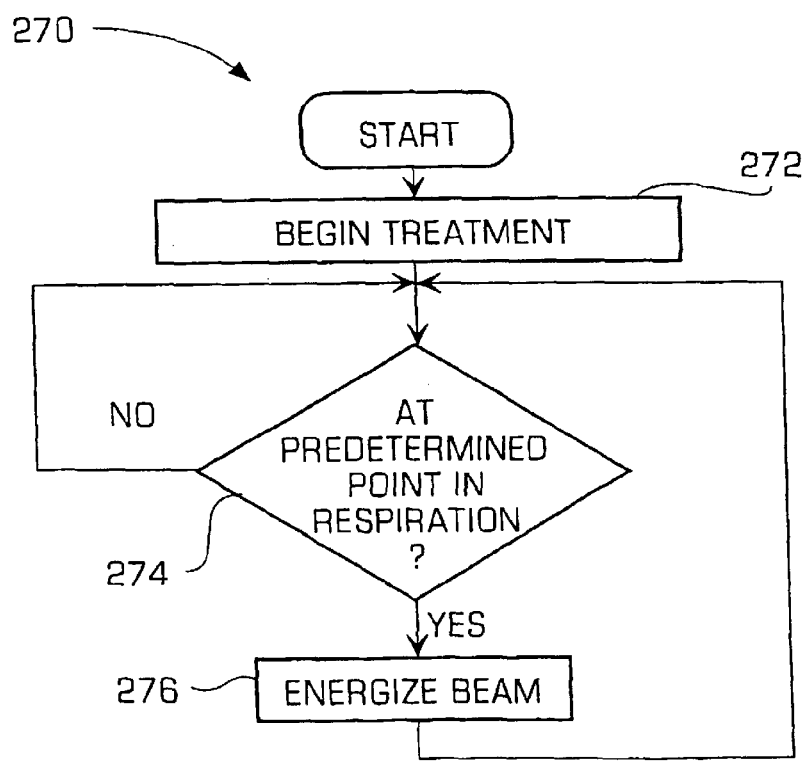
FIG. 8 is a flowchart illustrating a method for treating a patient with respiration tracking in accordance with the invention.

FIG. 8 is a flowchart illustration of a method 270 for energizing a diagnostic or treatment beam based on the respiration cycle in accordance with the invention. In step 272, the treatment is started and the respiration cycle of the patient is determined. In step 274, the system determines if at predetermined point in the respiration cycle has occurred and waits until the predetermined point has occurred. Once the predetermined point in the respiration cycle is reached, the system may energize the beam in step 276. Now, a second embodiment of the invention will be described.

FIG. 9 is a diagram illustrating a second embodiment of the frameless treatment system 150 in accordance with the invention. This embodiment of the invention is particular applicable to fiducial-less targeting of a target region wherein a surrounding region can be located, but the surrounding region does not have a fixed relationship with the target region (e.g., no bones are present) and respiration motion does not affect the position of the target region. An example of a target region for this embodiment is the prostate.

The system 150 may include the same elements as the prior embodiment as designated by like reference numerals such as the treatment table 102, the image recorder 104 and the diagnostic beam generator 106. As with the prior embodiment, the robot and the treatment beam generator are not shown. In this embodiment, a single diagnostic beam generator 106 may be used to further reduce the cost of the treatment system. In this embodiment, the system may further include a track 152 in which the diagnostic beam generator moves so that the diagnostic beam generator may be moved to different positions (see the diagnostic beam generator 106 in a first position 154 and the other positions shown by the phantom pictures of the generator) wherein the diagnostic beam generator is at a different non-zero angle with respect to the other positions. Thus, in this embodiment, the diagnostic beam generator 106 is moved from the first position 154 to other positions at periodic times in order to generate the images of the target region as described above. The embodiment may have similar elements as those shown in FIG. 5 and may also include a controller, to position the diagnostic beam generator, that may be controlled by the computer. Now, the method of treatment using the second embodiment will be described.

Figure 10:
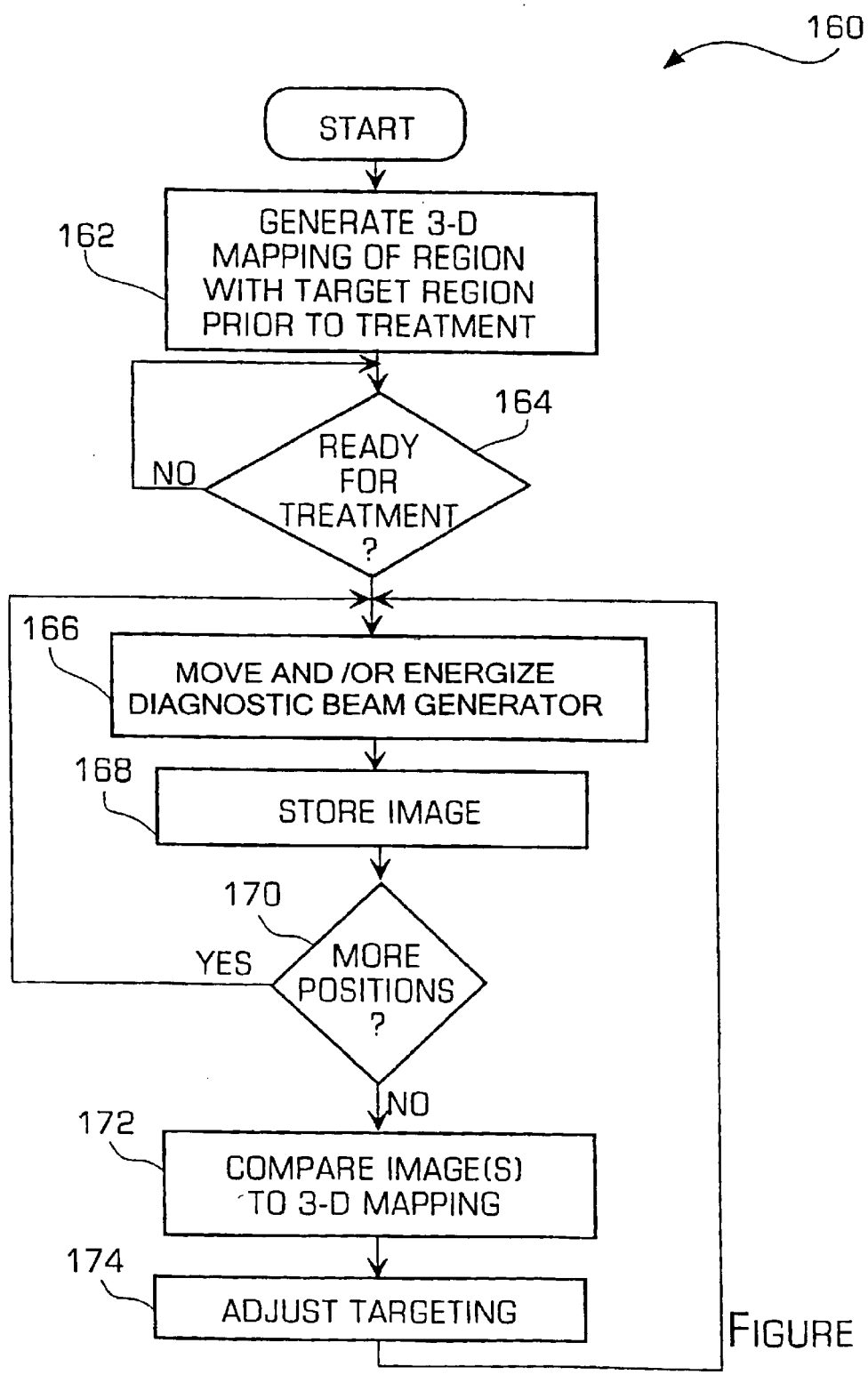
FIG. 10 is a flowchart illustrating a method for treatment in accordance with the invention using the system of FIG. 9.

FIG. 10 is a flowchart illustrating a method 160 for treatment in accordance with the invention using the system of FIG. 9. In step 162, a three-dimensional mapping of a region of the patient including the target region is generated prior to the treatment. The three-dimensional mapping may be done using typical equipment such as computer tomography or the like. The three-dimensional mapping of the region is stored in the storage device 118. The mapping shows the location of the target region with respect to other surrounding regions that may be seen in the mapping to locate the target region relative to the surrounding regions. For example, the target region may be a prostate tumor and the other surrounding regions may be the bladder. On the day of treatment, the patient may be positioned on the treatment bed as shown in FIG. 7. In step 164, the system may determine if the treatment can begin based on the status of the safety interlocks. If it is not safe to begin the treatment, then the method loops back to test the safety interlocks until a safe condition is indicated.

In step 166, a diagnostic beam generator is positioned along the track in the appropriate position and energized by the computer in order to generate an image on the recording device. In a preferred embodiment, the diagnostic beam generators is an x-ray generator and the image recorder is an amorphous silicon imager that generates an image in response to x-rays as is well known. The image generated by the first diagnostic beam in the image recorder may then be downloaded by the computer to the storage device attached to the computer in step 168 and the image recorder may be reset. In step 170, the method determines if there are any other positions for the diagnostic beam. If there are other positions for the diagnostic beam, the method loops back to step 166 to energize that generator at the other position, generate an image and download the image to the storage device. In this embodiment, the movement of the diagnostic beam generator along the track generates multiple images wherein each image is at a non-zero angle with respect to the other images. In accordance with the invention, the method sequentially energizes the diagnostic beam generator at different positions to generate the images in a time sequential manner. In accordance with the invention, repeated sequence of images from the diagnostic beam generator may be generated at periodic times so that the location of the target region at different times may be determined. The 2-D images generated by the diagnostic beams are processed to yield a CT-like image which may then be compared to the pre-operative 3-D mapping.

Once the diagnostic images are generated, the two or more images are compared to the three-dimensional pre-operative mapping as is well known to determine the location of the target region at the particular time in step 172. The comparison may again include the step of deformation as described above. In step 174, the targeting of the treatment beam is adjusted based on the comparison so that the treatment beam is always focused on the target region. If there are repeated diagnostic images generated, after each new set of images is generated, the images are compared to the mapping and the treatment beam targeting is adjusted to compensate for changes in the position of the target region. In this manner, the target region is accurately tracked so that the treatment beam is focused on the target region.

Figure 11:
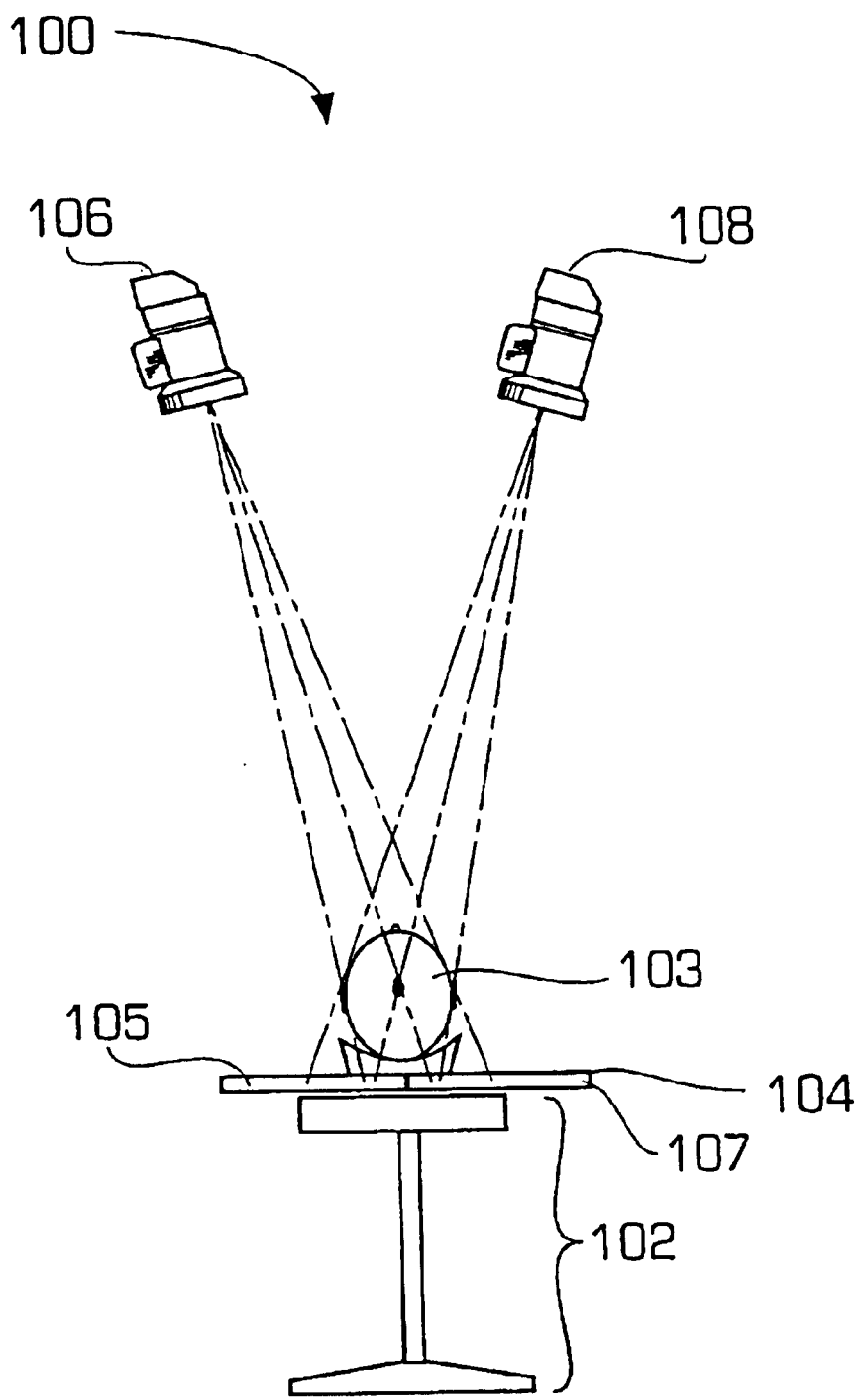
FIG. 11 is a diagram illustrating a third embodiment of the frameless treatment system in accordance with the invention.

FIG. 11 is a diagram illustrating another embodiment of the frameless treatment system 100 in accordance with the invention that may be particularly suited for treating target regions that have a fixed relationship to a fixed reference point, such as bones. Thus, this embodiment of the invention may be used for treating, for example, the spine of a patient or the brain of the patient since these target regions are near or surrounded by bones. The other embodiments of the invention described below may be particularly suited for the treatment of other target regions. In this figure, only one detector under the patient couch is used. The two diagnostic beams in this case may either be activated sequentially or the two beams may be activated simultaneously while projecting their respective images to a different portion of the single detector plate/camera. The simultaneous activation of the diagnostic beams is particularly useful when time-stamps are needed so that the exact time of a given 3-D position is known.

The treatment system 100 may include a patient treatment table or couch 102 on which a patient 103 may rest during the treatment. In the example shown, the brain of the patient is being treated. The treatment system may also include a diagnostic beam recording device 104 that may be located underneath the treatment table and underneath the patient and one or more diagnostic beam generators 106, 108 (two are shown in this example). The recording device 104 may record the images generated when each diagnostic beam device 106, 108 is energized. The recording device 104 may be any device that can be used to capture the image generated by the diagnostic beams. In a preferred embodiment, the recording device 104 may be the amorphous silicon plate that captures the x-ray beams being generated by the diagnostic beam generators 106, 108. The recording device 104 may be connected to a computer that controls the operation of the recording device and the diagnostic beam generators. The recording device in this embodiment may have a first portion 105 and a second portion 107 wherein the first diagnostic beam is captured by the first portion and the second diagnostic beam is captured by the second portion. Thus, the diagnostic beams may be simultaneously energized or may be sequentially energized.

In accordance with the invention, the diagnostic beam generators 106, 108 may be controlled by the computer to be energized at different predetermined time intervals or simultaneously so that each diagnostic beam generator is producing an image on the recording device at a different time or simultaneously. In addition, the diagnostic beam generators are located at different positions so that the diagnostic beams pass through the patient at different non-zero angles so that the angle between the two diagnostic beams is also non-zero which permits a two-dimensional image of the target region to be generated from the two images.

In operation, the first diagnostic beam generator 106 may be energized to emit a diagnostic beam that passes through the target region and generates an image on the recording device. The image developed by the recording device is then downloaded to the computer and the recording device is erased. Next, the second diagnostic beam 108 is energized and an image generated by the second diagnostic beam is received by the recording device. This image is also downloaded to the computer where it is stored with the first image. By comparing these diagnostic images in combination with the pre-operative 3-D CT scan or the like, the treatment beam (not shown) of the treatment system may be accurately targeted at the target region. For purposes of illustration, the treatment beam generator and the treatment beam robot are not shown in FIG. 11. The operation of this embodiment of the treatment system is described in more detail below with reference to FIG. 12.

Figure 12:
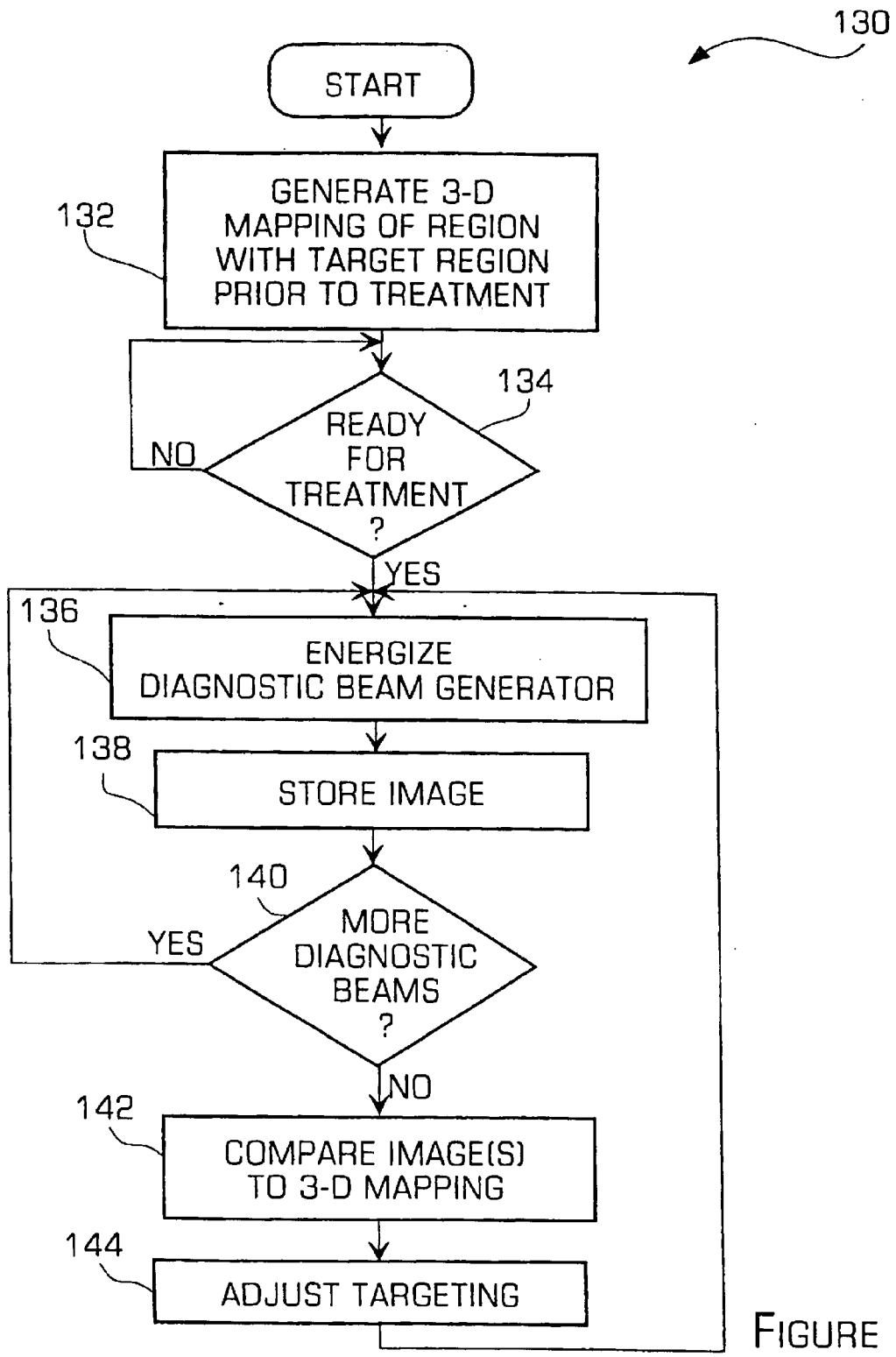
FIG. 12 is a flowchart illustrating a method for treatment in accordance with the invention using the system of FIG. 11.

FIG. 12 is a flowchart illustrating a method 130 for treatment in accordance with the invention using the system of FIG. 11. In particular, in step 132, a three-dimensional mapping of a region of the patient including the target region is generated prior to the treatment. The three-dimensional mapping may be done using typical equipment such as computer tomography or the like. The three-dimensional mapping of the region is stored in the storage device 118. The mapping shows the location of the target region with respect to other surrounding regions that may be seen in the mapping and appear on X-ray images made with the image recorder. For example, the target region may be a brain tumor and the other surrounding regions may be the skull bones. On the day of treatment, the patient may be positioned on the treatment bed as shown in FIG. 4. In step 134, the system may determine if the treatment can begin based on the status of the safety interlocks. If it is not safe to begin the treatment, then the method loops back to test the safety interlocks until a safe condition is indicated.

In step 136 when the treatment begins, a first diagnostic beam generator is energized by the computer in order to generate an image on the recording device. In a preferred embodiment, the diagnostic beam generators are x-ray generators and the image recorder is an amorphous silicon imager that generates an image in response to x-rays as is well known. The image generated by the first diagnostic beam in the image recorder may then be downloaded by the computer to the storage device attached to the computer in step 138 and the image recorder may be reset. In step 140, the method determines if there are any other diagnostic beams to be energized. If there are other diagnostic beams to energize, the method loops back to step 136 to energize that generator, generate an image and download the image to the storage device. In this embodiment, there may be two diagnostic beam generators that are at a predetermined non-zero angle with respect to each other. In accordance with the invention, the method sequentially energizes the diagnostic beam generators to generate the images from each of the diagnostic beams in a time sequential manner. In accordance with the invention, repeated pairs of images from the diagnostic beam generators may be generated at periodic times so that the location of the target region at different times may be determined.

Once the diagnostic images are generated, the two images are compared to the three-dimensional pre-operative mapping as is well known to determine the location of the target region at the particular time in step 142. In step 144, the targeting of the treatment beam is adjusted based on the comparison so that the treatment beam is always focused on the target region. If there are repeated diagnostic images generated, after each new set of images is generated, the images are compared to the mapping and the treatment beam targeting is adjusted to compensate for changes in the position of the target region. In this manner, the target region is accurately tracked so that the treatment beam is focused on the target region.

Figure 13:
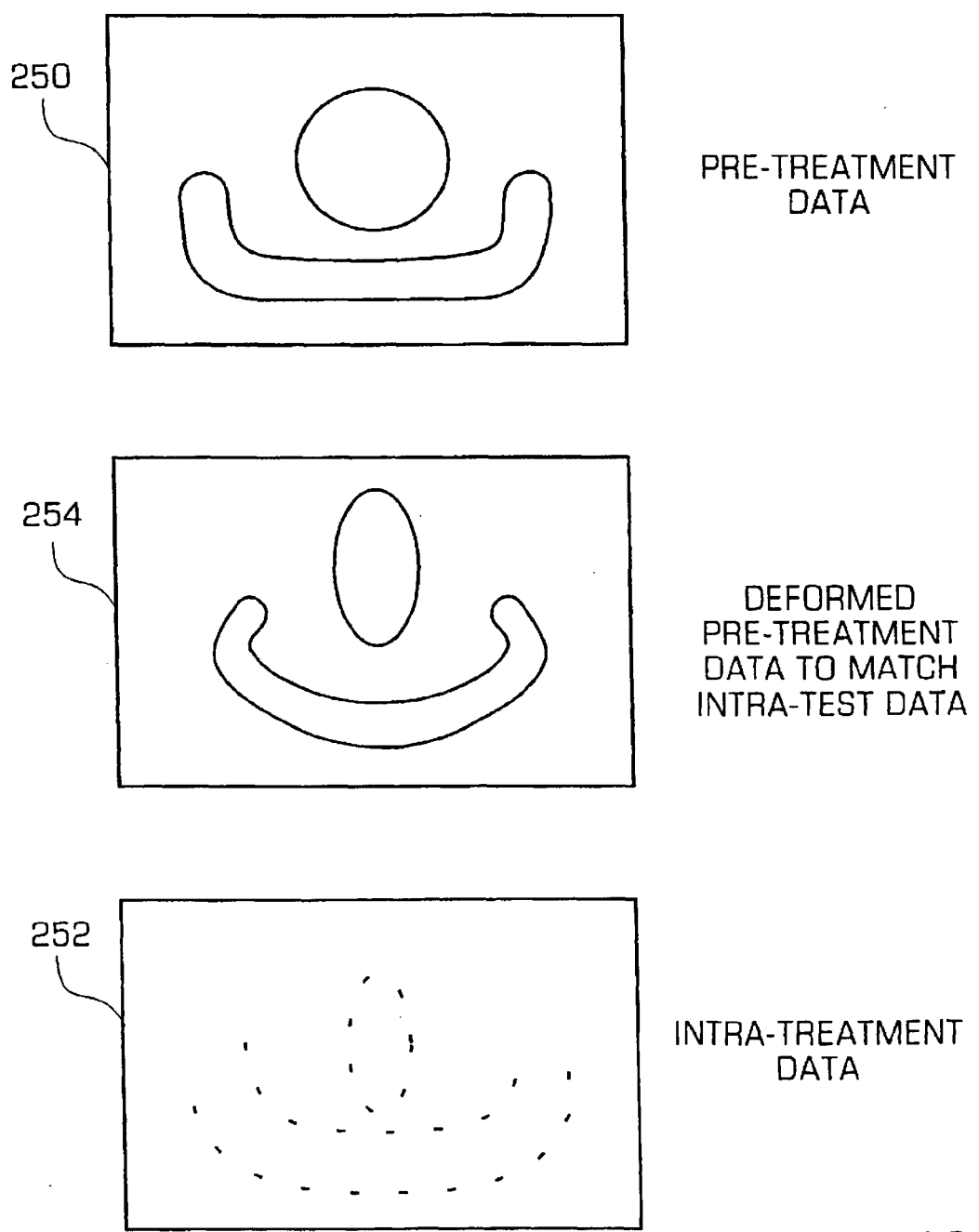
FIG. 13 illustrates the deformation of the pre-treatment and/or intra-treatment data to establish optimal correspondence to infer better target positions.

FIG. 13 illustrates a pre-operative image 250 and intra-treatment image data 252 generated by the diagnostic beams. As shown, the intra-treatment images generated by the diagnostic beams are less clear and it is difficult to make out all of the structures or even the target region in the image. The pre-operative image 250, on the other hand, is very clear and each structure of the body can be clearly seen. Therefore, in order to make it possible to infer the position of the target region from the intra-treatment images shown, the intra-treatment image is deformed, using various well known deformation techniques such as linear interpolation or warping, to form a deformed image 254 until the intra-treatment images and its structures form the best match with the pre-operative images. Once the deformation is completed, the position of the target region may be inferred from the position of the structures. This deformation technique may be used with all of the embodiments of the invention described above.

Although the above embodiments show a single diagnostic beam source being used, the invention is not limited to a single diagnostic beam source. In fact, the system may use five fixed sources that generate the diagnostic beams and two or more moving sources that generate the diagnostic beams. For the fixed sources, they may be activated at specific time points throughout the respiration cycle. More detailed information about the deformation model corresponding to respiratory motion may then be obtained as set forth in the U.S. patent application Ser. No. 09/270,404.

While the foregoing has been with reference to particular embodiments of the invention, it will be appreciated by those skilled in the art that changes in these embodiments may be made without departing from the principles and spirit of the invention, the scope of which is defined by the appended claims.

What is claimed is:

1. A system for treating a target region by directing a treatment beam towards the target region, comprising:
   a treatment beam generator for generating a radiosurgical treatment beam;
   one or more diagnostic x-ray beam generators for generating during treatment a plurality of diagnostic beams, each diagnostic beam being directed towards and through the target region, each diagnostic beam being generated from a different position so each diagnostic beam passes through the target region at a predetermined non-zero angle with respect to each other;
   at least one imagining device for receiving each the plurality of diagnostic beams after each diagnostic beam has passed through the target region, and for generating a 2-D diagnostic image of the target region from each received diagnostic beam; and
   a processor for synthesizing a relatively low clarity intra treatment 3-D image of the target region from said plurality of 2-D diagnostic images, and for comparing said synthesized 3-D image with a relatively high clarity pre-operative three-dimensional CT scan image to determine the position of the target region, so that said radiosurgical treatment beam can be continuously focused onto the target region.

2. A system in accordance with claim 1 further comprising a respiratory motion detection system for sensing the respiratory motion of the patient during the treatment so as to determine the respiratory cycle of said patient.

3. A system in accordance with claim 2, further comprising means for activating said one or more diagnostic x-ray beam generators at one or more predetermined points within said respiratory cycle.

4. A system in accordance with claim 1 further comprising means for generating the three-dimensional pre-operative CT scan image of the target region, and means for adjusting the targeting of a treatment beam in response to the comparison of the synthesized 3-D image with the three-dimensional pre-operative CT scan image so that said treatment beam can be continuously focused onto the target region.

5. The system of claim 4, wherein the adjusting means further comprises a computer-controlled robot for positioning the treatment beam.

6. A system in accordance with claim 4, wherein said three-dimensional pre-operative CT scan image of the target region comprises a CT (computer tomography) scan.

7. A system in accordance with claim 1 wherein comprising means for generating a plurality of diagnostic beams comprise one or more x-ray beam generators.

8. A system in accordance with claim 1, wherein the image receiver comprises an amorphous silicon image receiver.

9. A system in accordance with claim 1, wherein said treatment beam generator comprises an x-ray source having a linear accelerator.

10. A system in accordance with claim 1, wherein said processor further comprises means for deforming the pre-operative image so that the visible structures in the pre-operative image and the diagnostic beam images match, and means for determining the location of a target region based on the deformation.

11. A system in accordance with claim 1, wherein said processor further comprises means for deforming the diagnostic beam images so that the visible structures in the pre-operative image and the diagnostic beam images match, and means for determining the location of a target region based on the deformation.

12. A system in accordance with claim 1, wherein a means for synthesizing said 3-D image comprises means for processing said plurality of 2-D diagnostic images with one or more algorithms used in computed tomography.

13. A system in accordance with claim 1, further comprising a track that supports at least one diagnostic beam generator to move said diagnostic beam generator between a plurality of different positions at which each diagnostic beam is generated.

14. A method for treating a patient, comprising:
   generating a relatively high clarity three-dimensional pre-operative CT scan image of an anatomical region of the patient, said anatomical region including a target region to be treated by a radiosurgical treatment beam;
   generating during treatment a plurality of diagnostic x-ray beams from different positions and directing said diagnostic x-ray beams towards at least one image receiver and through said target region of the patient, so that each beams passes through the target region at predetermined non-zero angles with respect to each other;
   receiving said plurality of diagnostic x-ray beams from said at least one image receiver when the diagnostic x-ray beams have passed through the target region, so as to generate a plurality of 2-D diagnostic images, one for each diagnostic x-ray beam;
   synthesizing a relatively low clarity intra-treatment 3-D image from said plurality of 2-D diagnostic images; and
   comparing said sythesized 3-D image to the relatively high clarity three-dimensional CT scan image in order to control the movement of the treatment beam during the treatment so that said treatment beam remains focused onto said target region.

15. The method of claim 14, wherein said three-dimensional pre-operative CT scan mapping of said anatomical region comprises a three-dimensional computer tomography mapping of said anatomical region.

16. A method in accordance with claim 14, further comprising the step of sensing the respiratory motion of the patient during treatment so as to determined the respiratory cycle of said patient.

17. A method in accordance with claim 16, further comprising the step of activating one or more diagnostic x-ray beam generators at one or more predetermined points within said respiratory cycle so that each of said plurality of diagnostic beams is generated at a corresponding predetermined point in said respiratory cycle.

18. A method in accordance with claim 17, further comprising the step of activating a treatment beam generator at one or more predetermined points within said respiratory cycle so that said radiosurgical treatment beam is generated at said one or more predetermined points.

19. A method in accordance with claim 14, wherein the step of comparing the images further comprises the steps of deforming the pre-operative CT scan image so that the visible structures in the pre-operative CT scan image and the 3-D sythesized image match, and determining the location of a target region based on the deformation.

20. The method of claim 14, wherein comparing the images further comprises deforming the synthesized intra-treatment 3-D image so that the visible structures in the pre-operative CT scan image and the intra-treatment 3-D image match, and determining the location of a target region based on the deformation.

21. A method in accordance with claim 14, wherein the step of synthesizing said 3-D image comprises the step of processing said plurality of 2-D diagnostic images with one or more CT-like algorithms.

* * * * *